US008983854B2

(12) United States Patent
Park et al.

(10) Patent No.: US 8,983,854 B2
(45) Date of Patent: Mar. 17, 2015

(54) SCALE-TYPE NONCONSTRAINED HEALTH CONDITION EVALUATING APPARATUS AND METHOD

(75) Inventors: Kwang Suk Park, Seoul (KR); Jae Hyuk Shin, Seoul (KR)

(73) Assignee: SNU R & DB Foundation, Seoul (KR)

( * ) Notice: Subject to any disclaimer, the term of this patent is extended or adjusted under 35 U.S.C. 154(b) by 1046 days.

(21) Appl. No.: 12/425,955

(22) Filed: Apr. 17, 2009

(65) Prior Publication Data

US 2010/0210921 A1    Aug. 19, 2010

(30) Foreign Application Priority Data

Nov. 26, 2008  (KR) .......................... 10-2008-117883

(51) Int. Cl.
| | |
|---|---|
| *A61B 5/02* | (2006.01) |
| *A61B 5/11* | (2006.01) |
| *A61B 5/0205* | (2006.01) |
| *A61B 5/0402* | (2006.01) |
| *A61B 5/00* | (2006.01) |
| *G01G 19/414* | (2006.01) |

(52) U.S. Cl.
CPC ............ *A61B 5/1102* (2013.01); *A61B 5/0205* (2013.01); *A61B 5/0402* (2013.01); *A61B 5/6825* (2013.01); *A61B 5/6829* (2013.01); *G01G 19/4146* (2013.01)
USPC ............... 705/2; 600/300; 600/301; 600/527; 705/3

(58) Field of Classification Search
CPC ................................ A61B 5/021; A61B 5/024
USPC .................. 705/2, 3; 128/714; 600/500, 509, 600/300–301, 407, 527–529, 481, 483, 485
See application file for complete search history.

(56) References Cited

U.S. PATENT DOCUMENTS

| | | | | |
|---|---|---|---|---|
| 4,528,690 | A | * | 7/1985 | Sedgwick ........................ 381/67 |
| 4,836,215 | A | * | 6/1989 | Lee ................................ 600/527 |
| 4,838,275 | A | * | 6/1989 | Lee ................................ 600/483 |
| 5,002,060 | A | * | 3/1991 | Nedivi .......................... 600/484 |
| 5,620,003 | A | * | 4/1997 | Sepponen ..................... 600/527 |
| 5,995,858 | A | * | 11/1999 | Kinast ........................... 600/323 |
| 6,478,744 | B2 | * | 11/2002 | Mohler ......................... 600/485 |

(Continued)

FOREIGN PATENT DOCUMENTS

| | | | |
|---|---|---|---|
| KR | P0137272 B1 | 4/1998 | |
| KR | 10-2005-0079235 A | 8/2005 | |
| WO | WO 2010004502 A1 * | 1/2010 | ............... A61B 5/11 |

OTHER PUBLICATIONS

Korean Office Action for Korean Patent Application No. 10-2008-0117883 which corresponds to U.S. Appl. No. 12/425,955.

*Primary Examiner* — Hiep V Nguyen
*Assistant Examiner* — Teresa Williams
(74) *Attorney, Agent, or Firm* — LRK Patent Law Firm

(57) ABSTRACT

A scale-type nonconstrained health condition evaluating apparatus includes a load cell sensor for sensing a ballistocardiogram signal and a weight signal from a measured person, an electrocardiogram sensor for sensing an electrocardiogram signal from the measured person, and a signal processor for calculating at least one of the heart rate, normalized stroke volume force, blood pressure and equilibrium sense abnormality of the measured person from the ballistocardiogram, weight and electrocardiogram signals sensed by the load cell sensor and the electrocardiogram sensor.

12 Claims, 8 Drawing Sheets

(56) References Cited

U.S. PATENT DOCUMENTS

| | | | |
|---|---|---|---|
| 7,226,418 B2* | 6/2007 | Kim | 600/485 |
| 8,206,309 B2* | 6/2012 | Oh et al. | 600/485 |
| 2002/0193692 A1* | 12/2002 | Inukai et al. | 600/500 |
| 2004/0249258 A1* | 12/2004 | Tupin et al. | 600/407 |
| 2005/0004483 A1* | 1/2005 | Lin | 600/509 |
| 2005/0043645 A1* | 2/2005 | Ono et al. | 600/529 |
| 2005/0119711 A1* | 6/2005 | Cho et al. | 607/42 |
| 2006/0149139 A1* | 7/2006 | Bonmassar et al. | 600/300 |
| 2008/0161700 A1* | 7/2008 | Sachanandani et al. | 600/481 |
| 2008/0183232 A1* | 7/2008 | Voss et al. | 607/24 |
| 2008/0214942 A1* | 9/2008 | Oh et al. | 600/485 |
| 2009/0024044 A1* | 1/2009 | Virtanen et al. | 600/509 |
| 2009/0203972 A1* | 8/2009 | Heneghan et al. | 600/301 |
| 2010/0094147 A1* | 4/2010 | Inan et al. | 600/500 |

\* cited by examiner

ELECTROCARDIOGRAM

BALLISTOCARDIOGRAM

SCALE-TYPE NONCONSTRAINED HEALTH CONDITION EVALUATING APPARATUS AND METHOD

BACKGROUND OF THE INVENTION

1. Field of the Invention

The present invention relates to a scale-type nonconstrained health condition evaluating apparatus and method, and more particularly, to a scale-type nonconstrained health condition evaluating apparatus and method for measuring electrocardiogram, ballistocardiogram and weight signals from a measured person in a nonconstrained manner, calculating at least one of the heart rate, normalized stroke volume force, blood pressure and equilibrium sense abnormality of the measured person from the measured signals and outputting the calculation result.

2. Background of the Related Art

As widely known, cardiovascular disorders such as myocardial infarction, angina pectoris, cardiac failure, arteriosclerosis, embolism, hypertension, atherosclerosis and thrombus frequently occur in highly industrialized countries and become the biggest cause of death together with cancers and cerebrovascular disorders in advanced countries.

Recently, cardiovascular disorders have increased in Korea as income levels of people increase and food, closing and housing environments become westernized. Accordingly, a device for monitoring cardiovascular states of people only through simple measurement at home and indoors is required. However, conventional health devices adopt a method of flowing current to a measured person to measure the health condition of the person, and thus the devices may have bad influence on the body of the measured person and have limitations in providing information sufficient for monitoring cardiovascular disorders.

SUMMARY OF THE INVENTION

Accordingly, the present invention has been made in view of the above-mentioned problems occurring in the prior art, and it is a primary object of the present invention to provide a scale-type nonconstrained health condition evaluating apparatus and method for measuring an electrocardiogram signal, a ballistocardiogram signal and a weight signal from a measured person in a nonconstrained manner, calculating at least one of the heart rate, normalized stroke volume force, blood pressure and equilibrium sense abnormality of the measured person from the measured signals and outputting the calculation result.

To accomplish the above object of the present invention, according to the present invention, there is provided a scale-type nonconstrained health condition evaluating apparatus comprising a load cell sensor for sensing a ballistocardiogram signal and a weight signal from a measured person; an electrocardiogram sensor for sensing an electrocardiogram signal from the measured person; and a signal processor for calculating at least one of the heart rate, normalized stroke volume force, blood pressure and equilibrium sense abnormality of the measured person from the ballistocardiogram, weight and electrocardiogram signals sensed by the load cell sensor and the electrocardiogram sensor.

The scale-type nonconstrained health condition evaluating apparatus may further comprise a display that outputs the heart rate, normalized stroke volume force, blood pressure or equilibrium sense abnormality of the measured person, calculated by the signal processor.

The electrocardiogram sensor may include two bar-shaped exposed electrocardiogram electrodes and measure the electrocardiogram signal from both hands of the measured person. Otherwise, the electrocardiogram sensor may include two electrocardiogram electrodes that are attached to the top face of the load cell sensor to measure the electrocardiogram signal from both feet of the measured person.

The signal processor may comprise a signal amplifier for amplifying the ballistocardiogram and electrocardiogram signals sensed by the load cell sensor and the electrocardiogram sensor; a band pass filter for filtering only necessary bands of the ballistocardiogram and electrocardiogram signals amplified by the signal amplifier; an A/D converter for converting the ballistocardiogram and electrocardiogram signals filtered by the band pass filter into digital signals; and a computing unit for calculating at least one of the heart rate, normalized stroke volume force, blood pressure and equilibrium sense abnormality of the measured person from the weight of the measured person, sensed by the load cell sensor, the ballistocardiogram and electrocardiogram signals converted into the digital signals by the A/D converter.

The band pass filter may filter only 0.5 through 30 Hz components of the ballistocardiogram signal amplified by the signal amplifier and filter only 0.5 through 35 Hz components of the electrocardiogram signal amplified by the signal amplifier.

The computing unit may detect J waves from the ballistocardiogram signal converted by the A/D converter into the digital signal and calculate an interval of the J waves to obtain an average heart rate of the measured person.

The computing unit may synchronize the electrocardiogram signal with the ballistocardiogram signal based on the J waves of the ballistocardiogram signal to obtain an ensemble average so as to generate averaged electrocardiogram and ballistocardiogram signals, obtain the magnitude of the J waves from the averaged ballistocardiogram signal and calculate the normalized stroke volume force of the measured person according to the following equation.

$$\text{Normalized stroke volume force} = J\text{-wave magnitude}/\text{weight}.$$

The computing unit may detect an R-J interval from the averaged ballistocardiogram and electrocardiogram signals and calculate the blood pressure of the measured person from a regression equation derived from data about correlation of the R-J interval and a systolic blood pressure.

The computing unit may measure the extent of a variation of the ballistocardiogram signal and determine whether the sense of equilibrium of the measured person is abnormal from the measurement result.

The signal processor may identify the measured person through at least one of the calculated heart rate, normalized stroke volume force, blood pressure, equilibrium sense abnormality and weight of the measured person.

To accomplish the above object of the present invention, according to the present invention, there is provided a method for evaluating the health condition of a measured person in a scale-type nonconstrained health condition evaluating apparatus, which comprises a first step of sensing ballistocardiogram and weight signals from the measured person; a second step of sensing an electrocardiogram signal from the measured person; and a third step of calculating at least one of the heart rate, normalized stroke volume force, blood pressure and equilibrium sense abnormality of the measured person from the sensed ballistocardiogram, weight and electrocardiogram signals.

The method may further comprise the step of outputting the calculated heart rate, normalized stroke volume force, blood pressure or equilibrium sense abnormality after the third step.

The third step may comprise the steps of amplifying the sensed ballistocardiogram and electrocardiogram signals; filtering only necessary bands of the amplified ballistocardiogram and electrocardiogram signals; converting the filtered ballistocardiogram and electrocardiogram signals into digital signals; and calculating at least one of the heart rate, normalized stroke volume force, blood pressure and equilibrium sense abnormality of the measured person from the weight of the measured person and the ballistocardiogram and electrocardiogram signals converted into the digital signals.

To accomplish the above object of the present invention, according to the present invention, there is provided a method for calculating the blood pressure of a measured person by using an R-J interval, which comprises a first step of detecting the R-J interval from ballistocardiogram and electrocardiogram signals measured from the measured person and a second step of calculating the blood pressure of the measured person according to a regression equation derived from data about correlation of the R-J interval and a systolic blood pressure.

The first steps may comprises the steps of detecting J waves from the ballistocardiogram signal; synchronizing the electrocardiogram signal with the ballistocardiogram signal based on the detected J waves of the ballistocardiogram signal to obtain an ensemble average to as to generate averaged electrocardiogram and ballistocardiogram signals; and detecting the R-J interval from the averaged electrocardiogram and ballistocardiogram signals.

As described above, the present invention can easily monitor the cardiovascular health condition of a measured person at home and indoors all the time by using the scale-type apparatus. Furthermore, the health condition evaluating apparatus can safely measure the health condition because it uses a nonconstrained method that does not flow current to the measured person and only measures a vital signal.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Figure 1:
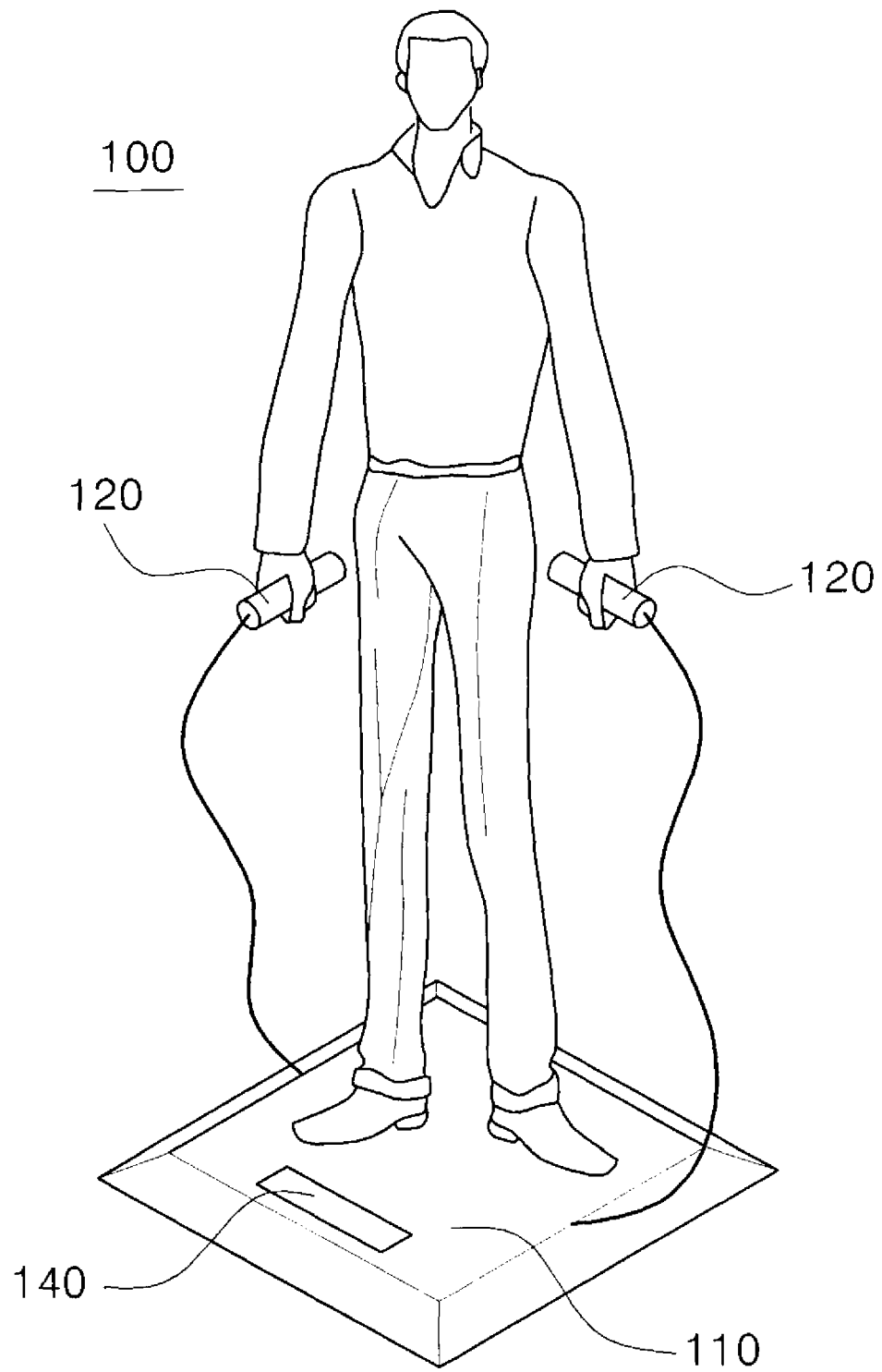
FIG. 1 illustrates a scale-type nonconstrained health condition evaluating apparatus according to a first embodiment of the present invention.

FIG. 1 illustrates a scale-type nonconstrained health condition evaluating apparatus 100 according to a first embodiment of the present invention.

Referring to FIG. 1, the scale-type nonconstrained health condition evaluating apparatus 100 includes a load cell sensor 110, an electrocardiogram sensor 120 and a display 140.

The load cell sensor 110 is located under the feet of a standing measured person. The load cell sensor 110 may be placed under the hips of the measured person when he or she sits and located under the chest of the measured person when he or she lies down. The weight of the person can be measured from a weight signal measured by the load cell sensor 110 and the weight signal can be amplified and filtered by a signal processor 130, which will be explained later, to obtain a ballistocardiogram signal according to a variation in the cardiovascular state of measured the person.

The electrocardiogram sensor 120 includes two bar-shaped exposed electrocardiogram electrodes that come in contact with the palms of the measured person to measure the electrocardiogram of the person.

The functions and detailed configurations of the load cell sensor 110, the electrocardiogram sensor 120 and the display 140 will be explained in detail with reference to FIG. 3.

Figure 2:
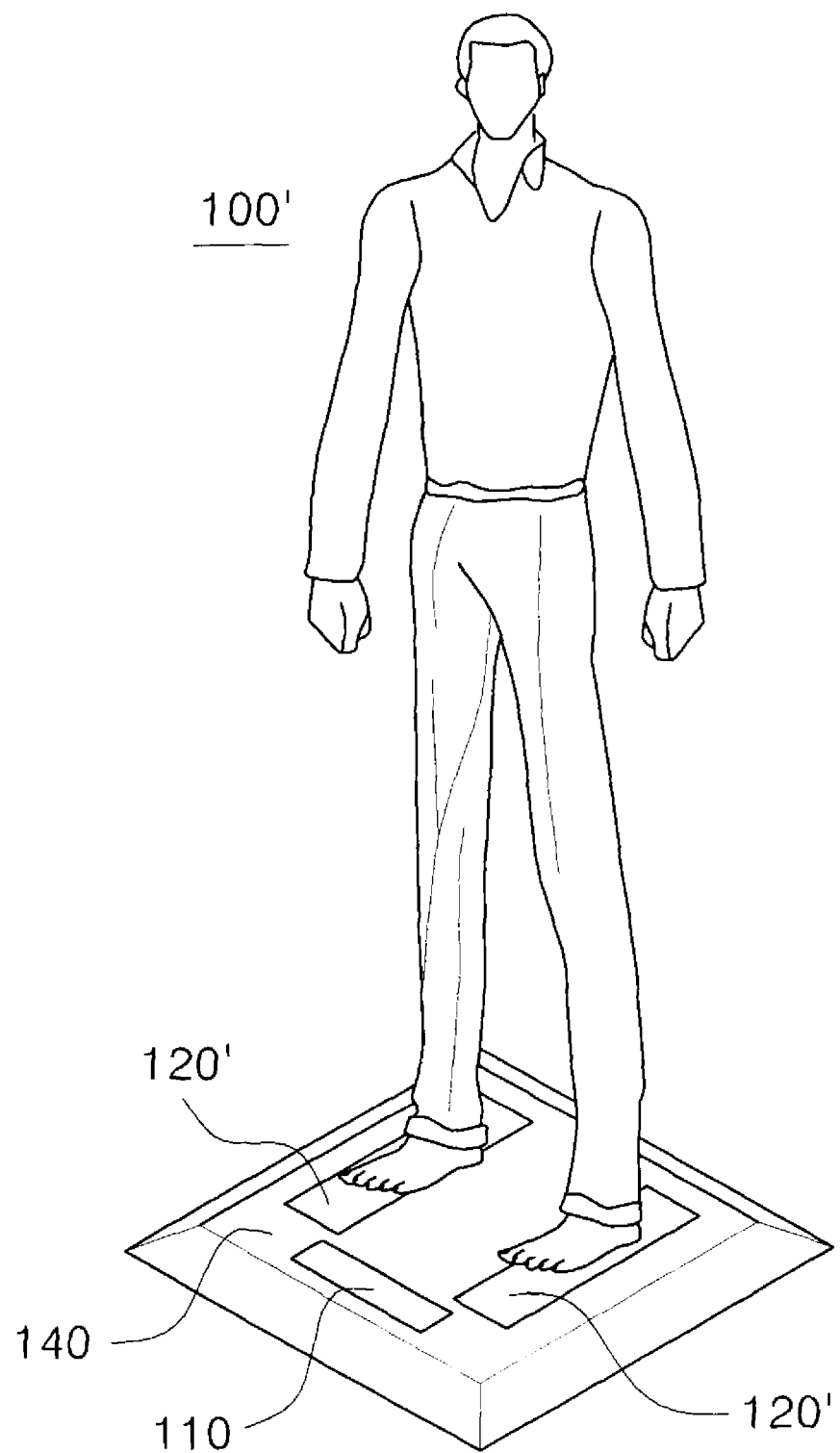
FIG. 2 illustrates a scale-type nonconstrained health condition evaluating apparatus according to a second embodiment of the present invention.

FIG. 2 a scale-type nonconstrained health condition evaluating apparatus 100' according to a second embodiment of the present invention.

Referring to FIG. 2, the scale-type nonconstrained health condition evaluating apparatus 100' has an electrocardiogram sensor 120' located in a position different from that of the scale-type nonconstrained health condition evaluating apparatus 100 according to the first embodiment of the present invention. Specifically, two electrocardiogram electrodes of the electrocardiogram sensor 120' are attached to the top face of the load cell sensor 110 to measure an electrocardiogram signal from both feet of the measured person.

Figure 3:
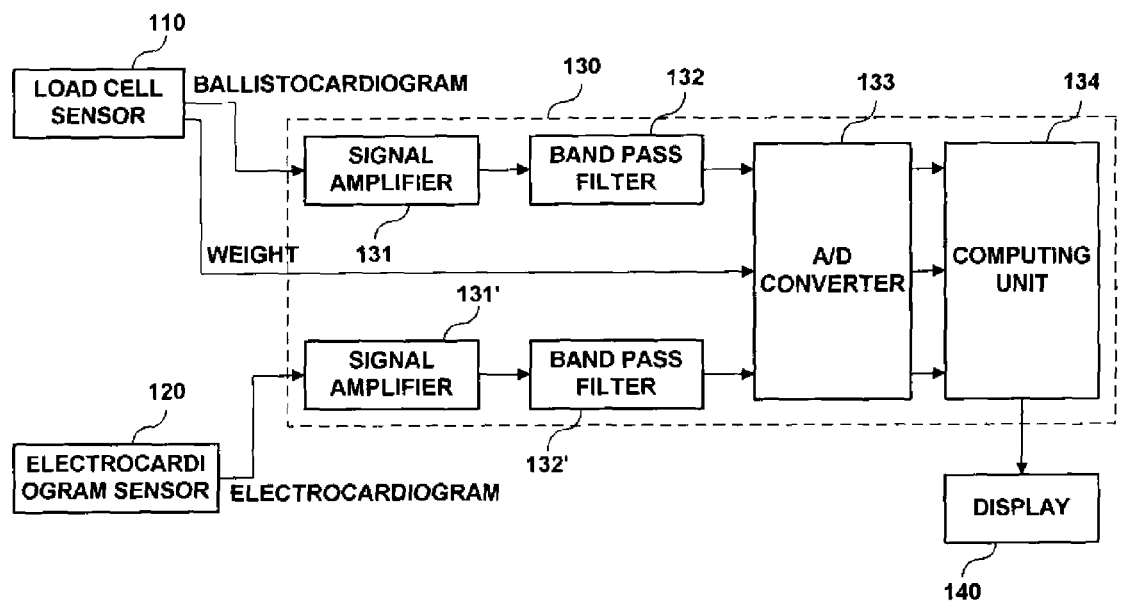
FIG. 3 is a block diagram of the scale-type nonconstrained health condition evaluating apparatus according to the present invention.

FIG. 3 is a block diagram of the scale-type nonconstrained health condition evaluating apparatus according to the present invention.

Referring to FIG. 3, the scale-type nonconstrained health condition evaluating apparatus according to the present invention includes the load cell sensor 110, the electrocardiogram sensor 120, the signal processor 130, and the display 140.

The load cell sensor 110 measures a ballistocardiogram signals and a weight signal from a measured person. The electrocardiogram sensor 120 measures an electrocardiogram signal from the measured person and may be constructed in such a manner that the electrocardiogram signal is measured from the hands or feet of the measured person, as described above.

The signal processor 130 calculates at least one of the heart rate, normalized stroke volume force, blood pressure and equilibrium sense abnormality of the measured person from the ballistocardiogram, weight and electrocardiogram signals measured by the load cell sensor 110 and the electrocardiogram sensor 120.

The display 140 outputs information on the at least one of the heart rate, normalized stroke volume force, blood pressure and equilibrium sense abnormality calculated by the signal processor 130 in a form recognizable by the sense of sight and hearing of the measured person.

The signal processor 130 will now be explained in more detail. The signal processor 130 includes a signal amplifier 131, a band pass filter 132, an A/D converter 133 and a computing unit 134.

The signal amplifier 131 amplifies the ballistocardiogram and electrocardiogram signals sensed by the load cell sensor 110 and the electrocardiogram sensor 120.

The band pass filter 132 filters only necessary bands of the ballistocardiogram and electrocardiogram signals amplified by the signal amplifier 131.

More specifically, the band pass filter 132 filters 0.5 through 30 Hz components of the amplified ballistocardiogram signal and filters 0.5 through 35 Hz components of the amplified electrocardiogram signal.

The A/D converter 133 converts the ballistocardiogram and electrocardiogram signals filtered by the band pass filter 132 into 1 kHZ and 16-bit digital signals.

The computing unit 134 calculates at least one of the heart rate, normalized stroke volume force, blood pressure and equilibrium sense abnormality of the measured person from the weight of the person, sensed by the load cell sensor 110, the ballistocardiogram and electrocardiogram signals converted into the digital signals by the A/D converter 133.

Figure 4:
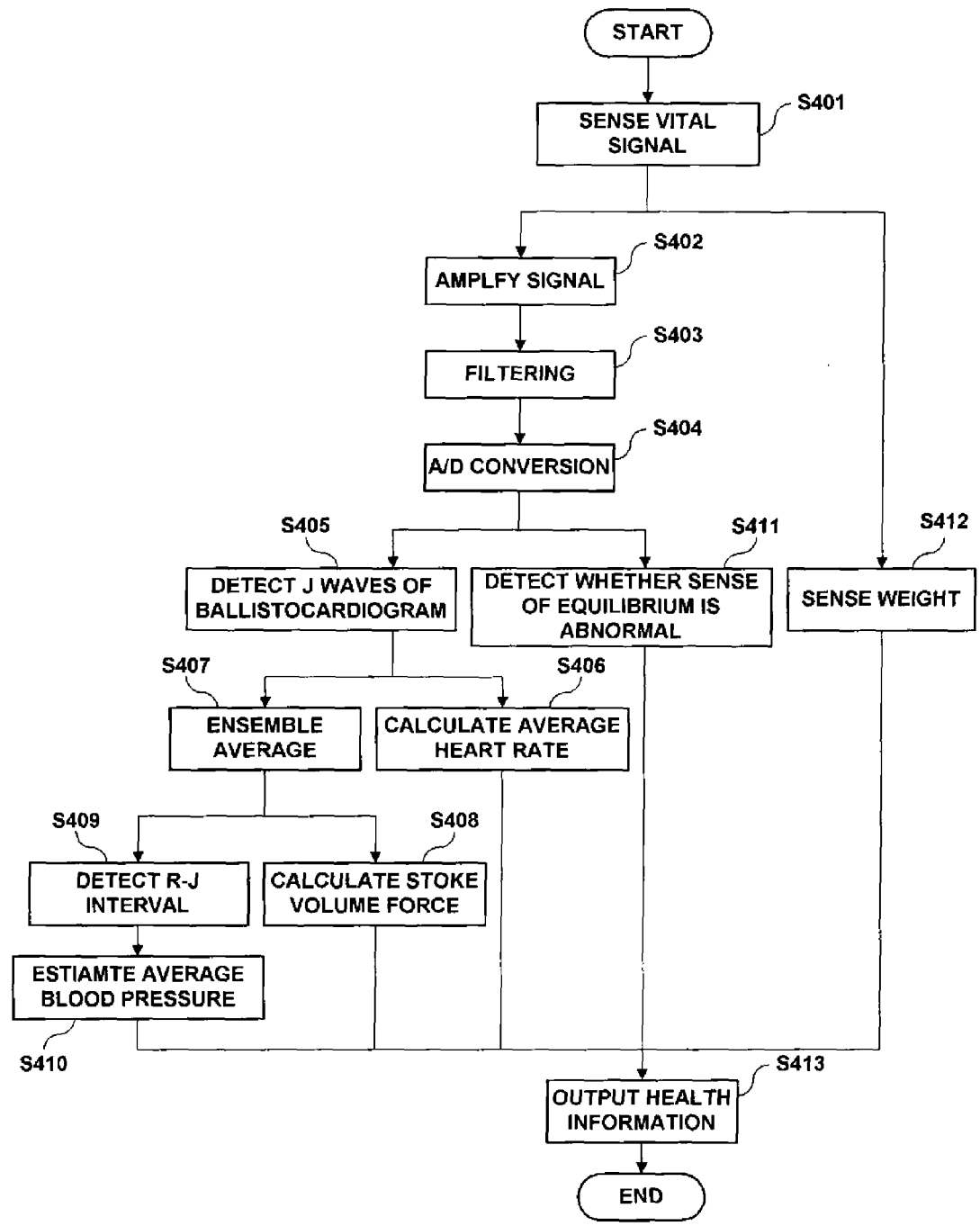
FIG. 4 is a flowchart of a nonconstrained health condition evaluating method according to the present invention.

FIG. 4 is a flowchart of a nonconstrained health condition evaluating method according to the present invention.

Figure 5:
FIG. 5 illustrates an electrocardiogram signal and a ballistocardiogram signal measured according to the present invention.
Figure 5:

A ballistocardiogram signal, an electrocardiogram signal and the weight of a measured person are sensed by the load cell sensor 110 and the electrocardiogram sensor 120 in step S401. The sensed ballistocardiogram and electrocardiogram signals are amplified and necessary bands thereof are filtered through the signal processor 130. Then, the filtered signals are converted into digital signals in steps S402, S403 and S404. FIG. 5 illustrates the ballistocardiogram and electrocardiogram signals converted into the digital signals through the aforementioned operation.

Subsequently, J waves are detected from the digital ballistocardiogram signal in step S405 and an interval of the J waves is calculated to obtain an average hear rate of the measured person in step S406.

Furthermore, a normalized stroke volume force and an average blood pressure of the measured person can be obtained from the digital ballistocardiogram and electrocardiogram signals.

Figure 6:
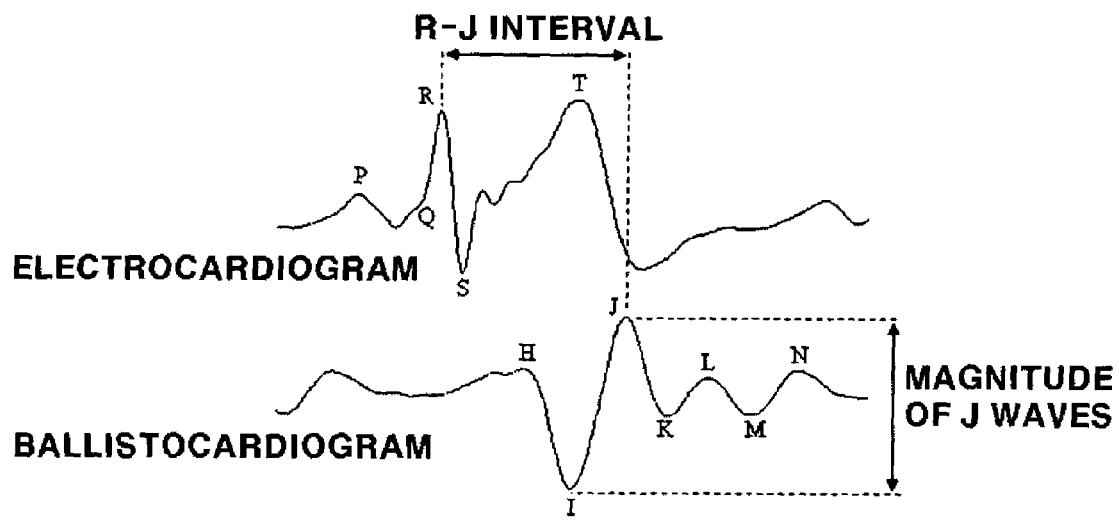
FIG. 6 illustrates averaged electrocardiogram and ballistocardiogram signals obtained through an ensemble average.

When the electrocardiogram signal is synchronized with ballistocardiogram signal based on the J waves of the ballistocardiogram signal, which are detected in step S405, to obtain an ensemble average in step S407, averaged ballistocardiogram and electrocardiogram signals from which an error due to a motion of the measured person or electrostatic noise has been removed can be obtained, as illustrated in FIG. 6. FIG. 6 illustrates the averaged ballistocardiogram and electrocardiogram signals obtained through the aforementioned operation.

When the magnitude of the J waves, which increases in proportion to cardiaoutput generated for a single stroke, is obtained from the averaged ballistocardiogram signal calculated in step S407 and divided by the weight according to the following equation, the normalized stroke volume force can be obtained in step S408.

$$\text{Normalized stroke volume force} = J\text{-wave magnitude}/\text{weight}$$

A step of obtaining the blood pressure of the measured person will now be explained.

An R-J interval is detected from the averaged ballistocardiogram and electrocardiogram signals, which are calculated in step S407, in step S409.

Figure 7:
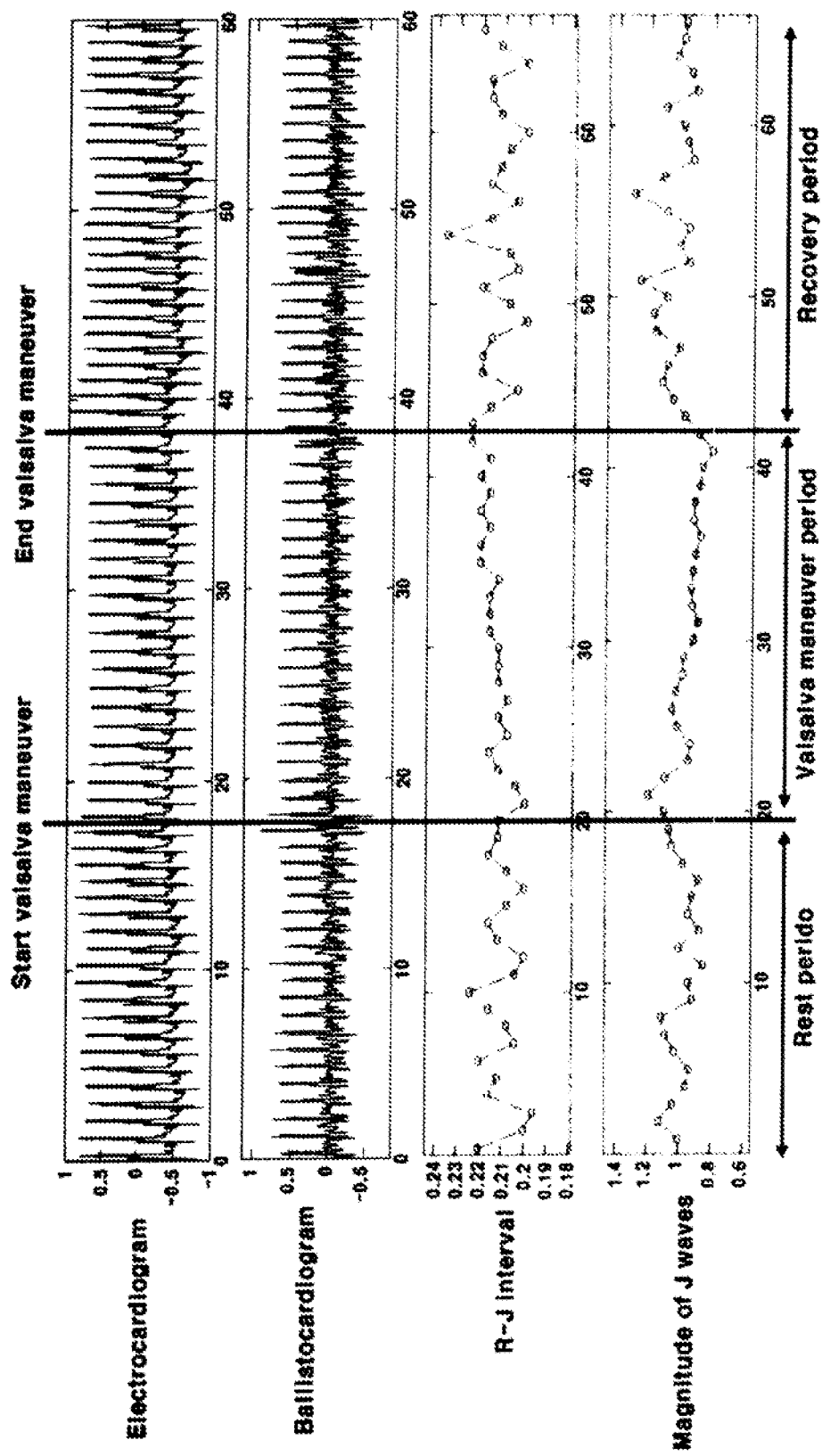
FIG. 7 is a graph illustrating a variation in R-J interval of a measured person when valsalva maneuver is performed.

The R-J interval reflects a cardiovascular state varied according to valsalva maneuver or other stimuli. For example, the R-J interval of the measured person increases when the valsalva maneuver is performed, as illustrated in FIG. 7.

Figure 8:
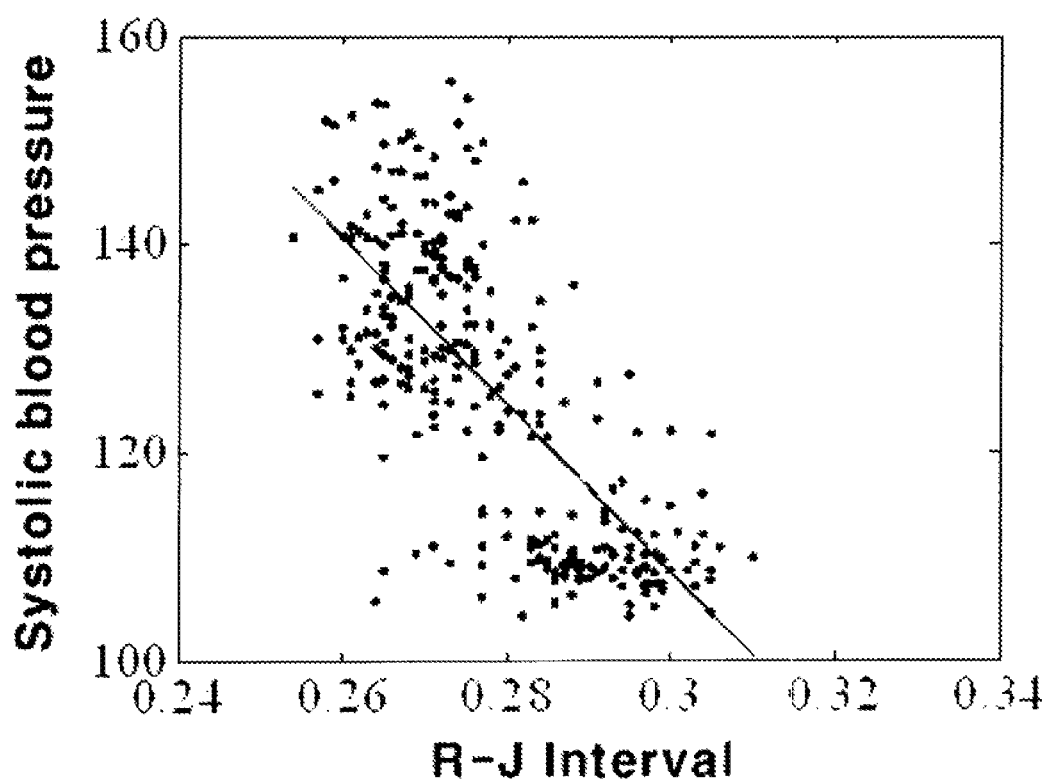
FIG. 8 is a graph illustrating correlation of an R-J interval and a systolic blood pressure.

Correlation of the R-J interval and a systolic blood pressure is as illustrated in FIG. 8 and correlation coefficient thereof is 0.73. Accordingly, if an expression that represents the correlation of the R-J interval and the systolic blood pressure is obtained using a linear regression equation, it is possible to calculate the blood pressure of the measured person by using only the R-J interval according to the following equation in step S410.

$$SBP(n) = -803.6091 \times RJI(n) + 349.6055$$

Here, SBP(n) represents an average blood pressure for n stokes of the measured person and RJI(n) denotes an average R-J interval.

The extent of a variation of the measured ballistocardiogram signal can be measured to determine how much the measured person stands in a stabilized pose and it is possible to check whether the equilibrium sensory organ of the measured person is abnormal by using the determination result in step S411.

Figure 9:
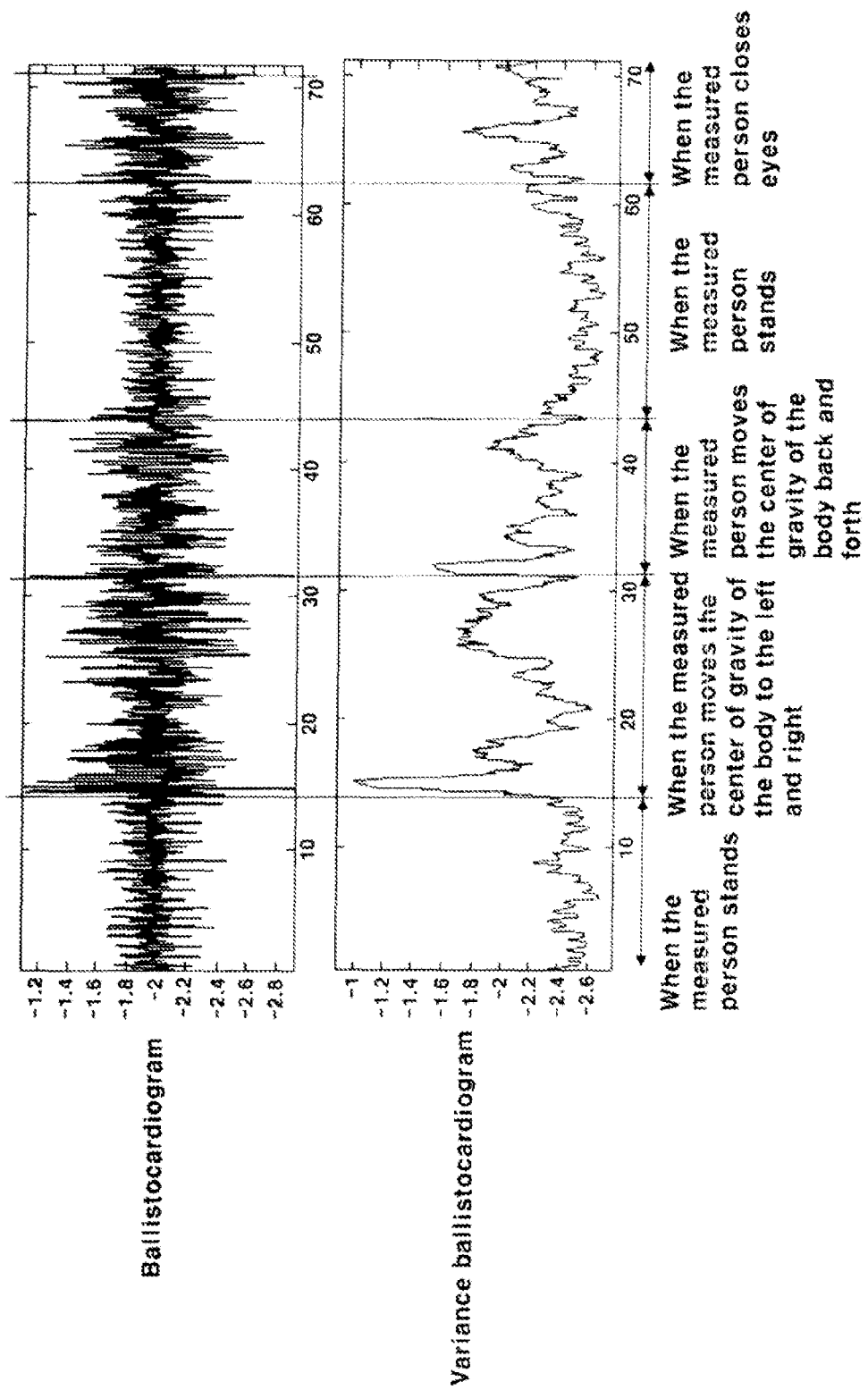
FIG. 9 is a graph illustrating a ballistocardiogram signal and variance of the ballistocardiogram signal according to a situation of a measured person.

FIG. 9 the ballistocardiogram signal and variance of the ballistocardiogram signal when the measured person stands on the load cell sensor, when the measured person moves the center of gravity of the body to the left and right, when the measured person moves the center of gravity of the body back and forth, and when the person closes his or her eyes and tries to maintain equilibrium. It can be known from FIG. 9 that the variance of the ballistocardiogram signal increases when the body of the person moves. Accordingly, it is possible to evaluate the extent of unstable motion over the entire test section.

The weight of the measured person can be measured from an unprocessed weight signal output from the load cell sensor 110 in step S412.

Furthermore, measured persons can be identified by using at least one of the heart rate, normalized stroke volume force, blood pressure, equilibrium sense abnormality and weight of each of the measured persons in an environment in which members of a family or ten constituent members or less use the scale-type nonconstrained health condition evaluating apparatus according to the present invention.

The information on the heart rate, normalized stroke volume force, blood pressure, equilibrium sense abnormality and weight of the measured person, which are calculated through the aforementioned operations, is output through the display in a form recognizable by the sense of sight and hearing of the measured person in step 413.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A scale-type nonconstrained health condition evaluating apparatus loaded on at least one hardware processor and comprising:
   a load cell sensor which is loaded on the at least one hardware processor and senses a ballistocardiogram signal and a weight signal from a measured person;
   an electrocardiogram sensor which is loaded on the at least one hardware processor and senses an electrocardiogram signal from the measured person; and
   a signal processor which is loaded on the at least one hardware processor and calculates at least one of the heart rate, normalized stroke volume force, blood pressure and equilibrium sense abnormality of the measured person from the ballistocardiogram, weight and electrocardiogram signals sensed by the load cell sensor and the electrocardiogram sensor,
   wherein the load cell sensor is configured to be placed under feet of the measured person in a standing position or under hips of the measured person in a sitting position,
   wherein the signal processor comprises:
   a signal amplifier which amplifies the ballistocardiogram and electrocardiogram signals sensed by the load cell sensor and the electrocardiogram sensor;
   a band pass filter which filters only necessary bands of the ballistocardiogram and electrocardiogram signals amplified by the signal amplifier;
   an A/D converter which converts the ballistocardiogram and electrocardiogram signals filtered by the band pass filter into digital signals; and
   a computing unit which calculates at least one of the heart rate, normalized stroke volume force, blood pressure and equilibrium sense abnormality of the measured person from the weight of the measured person, sensed by the load cell sensor, the ballistocardiogram and electrocardiogram signals converted into the digital signals by the A/D converter,
   wherein the computing unit synchronizes the electrocardiogram signal with the ballistocardiogram signal based on the J waves of the ballistocardiogram signal to obtain an ensemble average so as to generate averaged electrocardiogram and ballistocardiogram signals,
   wherein the computing unit detects an R-J interval from the averaged ballistocardiogram and electrocardiogram signals and calculates the blood pressure of the measured person from a regression equation derived from data about correlation of the R-J interval and a systolic blood pressure as follows:

$$SBP(n)=-803.6091 \times RJI(n)+349.6055$$

wherein SBP(n) represents an average blood pressure for n strokes of the measured person, and RJI(n) denotes an average R-J interval, and
   wherein a display displays the resulting detected R-J interval from the averaged ballistocardiogram and electrocardiogram signals and calculated blood pressure of the measured person from the regression equation for health compliancy.

2. The scale-type nonconstrained health condition evaluating apparatus according to claim 1, further comprising the display that outputs the heart rate, normalized stroke volume force, blood pressure or equilibrium sense abnormality of the measured person, calculated by the signal processor.

3. The scale-type nonconstrained health condition evaluating apparatus according to claim 1, wherein the electrocardiogram sensor includes two bar-shaped exposed electrocardiogram electrodes and measures the electrocardiogram signal from both hands of the measured person.

4. The scale-type nonconstrained health condition evaluating apparatus according to claim 1, wherein the electrocardiogram sensor includes two electrocardiogram electrodes that are attached to the top face of the load cell sensor to measure the electrocardiogram signal from both feet of the measured person.

5. The scale-type nonconstrained health condition evaluating apparatus according to claim 1, wherein the band pass filter filters only 0.5 through 30 Hz components of the ballistocardiogram signal amplified by the signal amplifier.

6. The scale-type nonconstrained health condition evaluating apparatus according to claim 1, wherein the band pass filter filters only 0.5 through 35 Hz components of the electrocardiogram signal amplified by the signal amplifier.

7. The scale-type nonconstrained health condition evaluating apparatus according to claim 1, wherein the computing unit detects J waves from the ballistocardiogram signal converted by the A/D converter into the digital signal and calculates an interval of the J waves to obtain an average heart rate of the measured person.

8. The scale-type nonconstrained health condition evaluating apparatus according to claim 1, wherein the computing unit obtains the magnitude of the J waves from the averaged ballistocardiogram signal and calculates the normalized stroke volume force of the measured person according to the following equation:

$$\text{Normalized stroke volume force}=J\text{-wave magnitude}/\text{weight}.$$

9. The scale-type nonconstrained health condition evaluating apparatus according to claim 1, wherein the computing unit measures the extent of a variation of the ballistocardiogram signal and determines whether the sense of equilibrium of the measured person is abnormal from the measurement result.

10. The scale-type nonconstrained health condition evaluating apparatus according to claim 1, wherein the signal processor identifies the measured person through at least one of the calculated heart rate, normalized stroke volume force, blood pressure, equilibrium sense abnormality and weight of the measured person.

11. A method for calculating blood pressure of a measured person by using an R-J interval, the method implemented in a scale-type nonconstrained health condition evaluating apparatus loaded on at least one hardware processor and comprising:
    detecting, by a signal processor loaded on the at least one hardware processor, the R-J interval from ballistocardiogram and electrocardiogram signals measured from the measured person; and
    calculating, by the signal processor, the blood pressure of the measured person according to a regression equation derived from data about correlation of the R-J interval and a systolic blood pressure as follows:

$$SBP(n)=-803.6091 \times RJI(n)+349.6055$$

wherein SBP(n) represents an average blood pressure for n strokes of the measured person, and RJI(n) denotes an average R-J interval,
    wherein the scale-type nonconstrained health condition evaluating apparatus is configured to be placed under feet of the measured person in a standing position or under hips of the measured person in a sitting position.

12. The method according to claim 11, wherein the detecting the R-J interval comprises:

detecting J waves from the ballistocardiogram signal;
synchronizing the electrocardiogram signal with the ballistocardiogram signal based on the detected J waves of the ballistocardiogram signal to obtain an ensemble average to as to generate averaged electrocardiogram and ballistocardiogram signals; and
detecting the R-J interval from the averaged electrocardiogram and ballistocardiogram signals.

* * * * *